(12) United States Patent
Irion

(10) Patent No.: US 6,450,950 B2
(45) Date of Patent: *Sep. 17, 2002

(54) ENDOSCOPE HAVING STEREO-LATERAL-VIEW OPTICS

(75) Inventor: Klaus Irion, Emmingen-Liptingen (DE)

(73) Assignee: Karl Storz GmbH & Co. KG (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 2 days.

(21) Appl. No.: 09/174,255

(22) Filed: Oct. 16, 1998

Related U.S. Application Data

(63) Continuation of application No. 08/877,372, filed on Jun. 17, 1997, now abandoned, which is a continuation of application No. 08/454,144, filed as application No. PCT/DE93/01187 on Dec. 11, 1993, now abandoned.

(30) Foreign Application Priority Data

Nov. 12, 1992 (DE) ............................... 42 41 938

(51) Int. Cl.⁷ .......................... A61B 1/05; A61B 1/005
(52) U.S. Cl. ................. 600/170; 600/114; 600/111; 600/166; 600/143; 600/151; 600/146
(58) Field of Search ................. 600/111, 166, 600/129, 136, 143, 170, 182, 114, 151, 146; 348/65, 42, 45, 46, 47; 385/117, 119

(56) References Cited

U.S. PATENT DOCUMENTS 3,253,524 A    5/1966    Ashizawa et al.
3,520,587 A    7/1970    Tasaki et al.
3,534,729 A    10/1970   Sakamoto
3,889,662 A    6/1975    Mitsui
4,862,873 A    9/1989    Yajima et al.
4,873,572 A    10/1989   Miyazaki et al.
4,926,257 A    5/1990    Miyazaki
4,941,457 A    7/1990    Hasegawa
5,025,804 A *  6/1991    Kondo ...................... 600/146
5,063,441 A    11/1991   Lipton et al.
5,101,269 A    3/1992    Shelley et al.
5,114,402 A    5/1992    McCoy
5,305,098 A    4/1994    Matsunaku et al.
5,381,784 A    1/1995    Adair
5,489,256 A    2/1996    Adair
5,522,789 A    6/1996    Takahashi

FOREIGN PATENT DOCUMENTS

JP    60-232524    11/1985
JP    63-201618    8/1988

* cited by examiner

Primary Examiner—John P. Leubecker
(74) Attorney, Agent, or Firm—St. Onge Steward Johnston & Greens LLC

(57) ABSTRACT

An endoscope having an endoscope shaft at the distal end of which a solid state image-recording system is disposed which is designed in the manner of lateral-view optics.

The image-recording system has at least two image recorders, built in a distal region of the endoscope shaft in such a manner that the viewing directon of the solid state image-recording system being approximately parallel to the axis of a proximal part of the endoscope shaft in one position and being perpendicular to it in another position automatically assumed by the distal region.

18 Claims, 4 Drawing Sheets

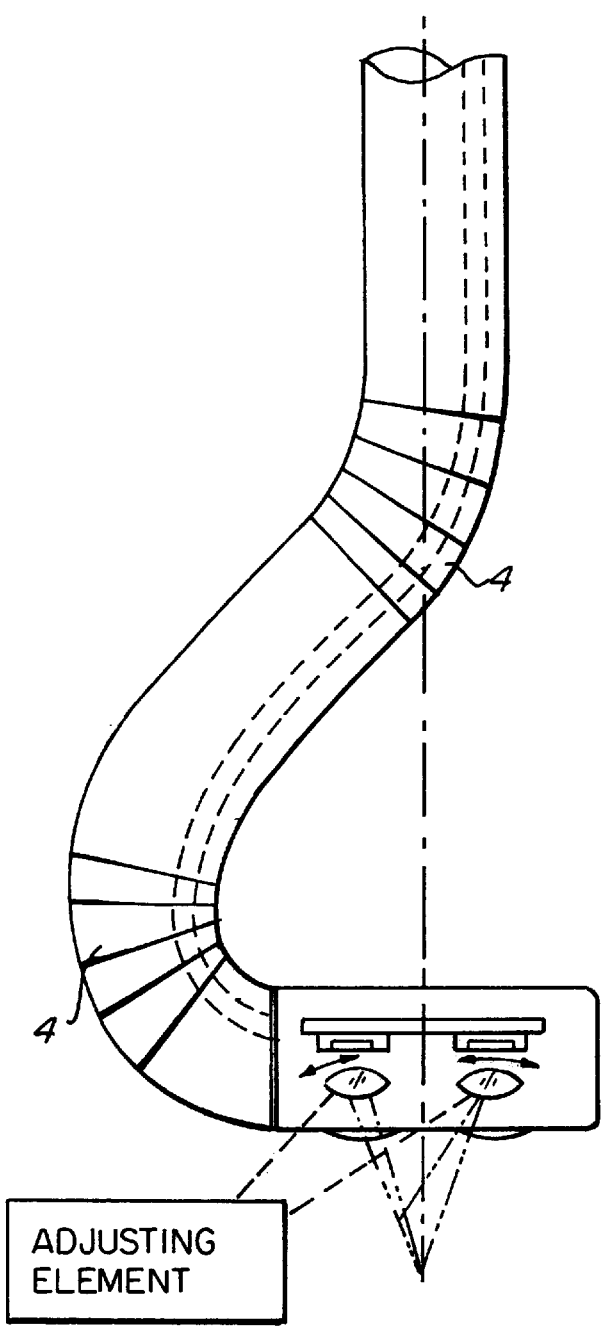
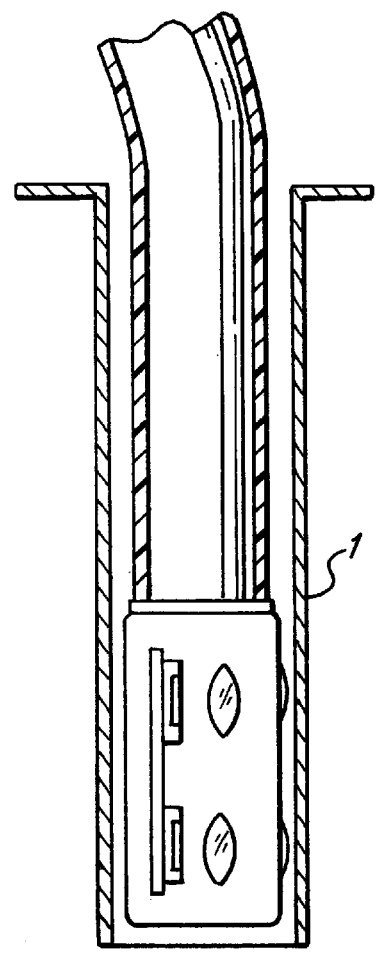
FIG. 3a
FIG. 3b

ENDOSCOPE HAVING STEREO-LATERAL-VIEW OPTICS

CROSS REFERENCE TO RELATED APPLICATION

This is a continuation of U.S. application Ser. No. 08/877,372, filed Jun. 17, 1997, now abandoned, which is a continuation of application Ser. No. 08/454,144, filed Jun. 9, 1995, now abandoned, which is a 371 of PCT/DE93/01187 filed on Dec. 11, 1993, the subject matter of which are incorporated by reference herein.

DESCRIPTION

1. Technical Field

The present invention relates to an endoscope having an endoscope shaft at the distal end of which is disposed a solid state image-recording system designed in the manner of lateral-view optics.

2. State of the Art

The surgical use of endoscopes has meanwhile proven to be quite successful and is in many cases, in addition to the conventional surgical techniques, a minimally invasive alternative procedure that has the advantage of being much less taxing to the patient and of shortening recovery time considerably. Apart from application in incorporal manipulation, respectively using suited endoscopic instruments for treatment of diseased parts of the body, endoscopes predominantly find use as a means of viewing and examining cavities in the human body.

In addition to the hitherto known, conventional rigid rod lens endoscopes, which only possess a single optical viewing channel and with which the surgeon receives only a two-dimensional image of the viewing area, there are known endoscopes that, using stereoscopic optical systems, permit reproduction of the surroundings of the surgery region including its spatial configuration.

The first considerations involving spatial viewing with the aid of endoscopes, the so-called stereo endoscopes, are based on the 1904 German patent DE 16 49 66, pertain to two separate, optical viewing paths which permit viewing an object opposite the distal end of the endoscope from two different directions. The proximal part of the endoscope is connected to a double eyepiece which simultaneously permits viewing the object with both eyes.

In addition to solely visual observation by the surgeon, for a number of reasons, it is desirable and even necessary in minimal-invasive endoscopic surgical techniques to realize the representation of the surgery area using video technology via a camera-monitor unit. Furthermore, the endoscopic procedure can be stored using video technology in such a manner that exact viewing is possible even following surgery. In this context, the described, conventional, optical stereo-endoscopic system requires that the two separate optical viewing systems each be connected at their proximal end to a camera system. These types of connection arrangements, however, in some instances demand very complex adjustments, therefore making handling the endoscope significantly more cumbersome. Moreover, the optical elements, respectively rod lenses in the endoscopes of the described, optical stereo systems possess a certain amount of mobility, which makes it impossible to prevent system-related blurriness at least not in adjusting the system.

As an alternative to conventional image transmission between the distal end and the proximal end of the endoscope with the aid of optical components (imaging lenses, optical fiber systems, i.a.), video image recorders, such as by way of illustration CCD-chips, are increasingly coming into use. For this reason, it has been often proposed to place in the image plane of the lenses disposed at the distal end of the endoscope an image recorder that is connected to a supply unit disposed at the proximal endoscope end by means of a transmission system instead of the conventional optical transmission systems. Concerning this, by way of example, reference is made to U.S. Pat. Nos. 4,235,447 and 4,261,344.

Therein solid state image-recording devices are widely employed, and of them the charge-coupled sensor types respectively CCD arrays seem to be the most suited.

Placing image-recording systems of this type at the distal end has the advantage, ie. that image transmission from the distal end to the proximal end of the endoscope can be carried out electronically, i.e., the signal transmission occurs via corresponding electric lines. This ensures more flexible endoscope guidance without optical distortions. Moreover, the considerable cost of the optical rod lenses is eliminated, permitting cheaper production of "electronic viewing endoscopes".

U.S. Pat. Nos. 4,699,125 and 4,926,257 deal with such types of endoscopes at which distal end image-recording systems are provided which are essentially composed of a lens and a solid state image-recording element, preferably a CCD array.

Furthermore, comparable electronic endoscopes are described in the following printed publications: U.S. Pat. Nos. 5,050,584, and 4,989,586 as well as DE-OS 38 06 190.

In the mentioned endoscopes, a semiconductor image recorder is placed in the image plane of the lens disposed at the distal end in such a manner that the light-sensitive sensor area forms a 90° angle with the axis of the endoscope. Reduction of the cross section of the endoscope in the distal region, therefore, is limited at least due to the currently smallest possible dimensioning of solid state image-recording sensors.

As an alternative to the so-called straight-ahead view endoscopes like the ones described in the mentioned state of the art, the lateral-view endoscopes having surface sensors which are aligned parallel to the axis of the endoscope offer major minimization of the cross section of the endoscope. Devices of this type are described in U.S. Pat. Nos. 4,685,451, and 4,562,831 as well as the German A-document DE 32 33 924. Lateral-view endoscopes whose view is aligned perpendicular to the axis of the endoscope and therefore are also aligned for insertion of the endoscope are primarily for gastroenterological viewing and examinaton of the duodenum and further treatment in the gall duct, which is practically at a 90° angle to the duodenum. Although this construction reduces the cross section of the endoscope, the surgeon is unable to view the region into which the endoscope is inserted in the direction of movement.

Contrary to electronic endoscopes which only have a single image-recording system, the German A-document DE 38 06 190 describes electronic endoscopic devices each having two imaging devices which, using solid state image recorders, permit the surgeon to gain a spatial impression of the viewing region of the endoscope. Although placing the image-recording systems in pairs in the straight-ahead viewing direction at the distal end of the endoscope grants the surgeon a viewing region which lies immediately before the tip of the endoscope and therefore permits controlled movement of the endoscope into the inside of the body, due to the necessity of working with as small as possible endoscope diameters, the spacing of the image recorder systems, the so-called stereo base, selected cannot be very large. However, this diametrically opposes the possibility of increasing the spatial visual impression and therefore a large as possible stereo base. Moreover, while maintaining a small as possible endoscope diameter, solid state image sensors having very small dimensions and therefore worse resolution can be utilized in this arrangement.

DE 39 21 233.5 describes, among other things, in FIG. 4, an electronic stereo endoscope in straight-ahead viewing. For this purpose, two independently movable image-recording systems are pivoted out of the co-axial position laterally to the side of the endoscope in such a manner that the stereo base can be enlarged considerably. The laterally pivotable folding mechanism of both image-recording systems makes it possible to meet the requirement of having an as small as possible endoscope cross section. Although the proposed solution offers the surgeon a spatial impression of the viewing area in the straight-ahead direction, it does not allow further degrees of freedom. Moreover, the exact positioning of both recording systems in relation to each other is a source of problems.

SUMMARY OF THE INVENTION

The object of the present invention is to further improve an endoscope having an endoscope shaft at the end of which a solid state image-recording system is disposed which is designed in the manner of lateral-view optics in such a way that the most optimum possible spatial impression of a lateral field can be obtained with the smallest possible endoscope cross section. Furthermore, three-dimensional viewing should include as much of the whole cavity into which the stereo endoscope is inserted as possible. The surgeon should be given an as simple as possible to operate viewing tool that, by way of illustration, completely obviates the necessity of adjusting the optics during use and that largely simplifies handling in such a way that there is never any difficulty in spatial orientation. Moreover, as large as possible image sensors having respectively high image resolution should be employed.

The present invention is based on the fundamental idea that the distal end of a lateral-view endoscope that is provided with at least two image recorders assumes in one position the lateral viewing direction and in the second position the straight-ahead viewing direction. By changing the viewing direction of the image-recording system by at least 90° C., the whole cavity can be viewed, by way of illustration, by additionally turning the endoscope about its longitudinal axis.

An element of the present invention is that the endoscope having a solid state image recording system, which is designed in the manner of lateral view optics, at its distal end is provided with at least two image recorders. In addition, the endoscope shaft can be deflected in the distal region in such a manner that the viewing direction of the solid state image-recording system can be aligned approximately parallel to the axis of the proximal part of the endoscope shaft. Another invented element is that the viewing direction of the solid state image-recording system can be disposed approximately coaxially to the axis of the proximal part of the endoscope shaft.

In other words, the overall inventive idea is to realize a stereo image-recording endoscope with a smallest possible endoscope shaft cross section for insertion into a cavity as well as to provide the largest possible stereo base while at the same time employing large-surface solid state image sensors with high resolution in order to ensure a distinct three-dimensional visual impression. The image-recording systems are provided in the distal region of the endoscope shaft in the lateral viewing direction in such a manner that the light-sensitive solid state image sensors are disposed in a row in the longitudinal axis of the endoscope. This has the advantage that the smallest cross section of the endoscope shaft is independent of both dimensions of an image sensor, but rather is only dependent on the lateral side of the sensor, thereby permitting as small as possible dimensioning of the endoscope cross section.

Once the endoscope has been inserted into the cavity to be viewed, according to the present invention, the viewing unit attached to the distal end of the endoscope can be switched from a lateral view direction to a second position which permits straight-ahead viewing. In order to make it easier for the surgeon to handle the endoscope, a defined change of position of the endoscope shaft from lateral view to straight-ahead view and vice-versa is provided. This factilitates handling considerably for the surgeon and simplifies coordination between the lateral-viewing direction and the straight-ahead direction. In this manner, orientation inside the cavitiy is improved by means of the two provided viewing-direction settings.

Of course, depending on the application, continuous movement of the endoscope shaft in several directions is also possible.

The present invention permits a viewing direction, which is disposed coaxially to the longitudinal axis of the endoscope, of the deflected endoscope shaft in the distal region in such a manner that, due to a 90° deflection relative to the longitudinal axis of the endoscope, the solid state image-recording system is quasi foldable in the straight-ahead direction. The discrete deformation of the endoscope shaft can be executed with the aid of a component provided in the distal region of the endoscope shaft which preferably is composed of a material having a thermal or mechanical memory capacity. For this purpose, in the insertion step, the endoscope shaft, which is provided with a rigid and a flexible part, is inserted into the cavity through a longitudinal trocar tube. If the flexible part of the endoscope shaft in the cavity emerges from the trocar tube, it automatically assumes its prescribed shape which is provided in such a manner that the image-recording system is preferably oriented in the straight-ahead direction.

This deflection of the endoscope shaft in the distal region can also occur in a controlled manner by means of Bowden wires or controllable joints, which can be operated manually or via an engine provided in the flexible part of the endoscope shaft.

In addition to being able to deflect the endoscope shaft in the distal region 90° permitting spatial viewing parallel to the longitudinal axis of the endoscope but not coaxially thereto, an element of the present invention is that it provides for another possible deflection of the endoscope shaft in the distal region which provides for viewing in spatial quality coaxially to the axis of the proximal part of the endoscope shaft.

The preceding viewing variant has the additional advantage that the surgeon receives a spatial visual impression of the viewing field through the endoscope which is immediately before the distal region in the thrust direction of the endoscope and therefore is largely coaxial to the longitudinal axis of the endoscope.

Handling the endoscope having a coaxial arrangement of the solid state image-recording system in the straight-ahead direction is similar to that of conventional rod lens endoscopes. This endoscopic solution obviates having to get accustomed to working with other imaging properties.

This distal arrangement of the solid state image-recording system is already advantageous with only one image recorder.

The use of stereo endoscopes of this type having an as large as possible stereo base for gaining an intensive spatial visual impression has the primary purpose of permitting the surgeon to improve his assessment of spatial distances. Especially, the handling of other endoscopic instruments for incorporal treatment in the vision cone of the stereo endoscope is decisively simplified by the spatiality of the visual impression. Thus, the surgeon is able to work with at least two instruments inserted into the cavity in such a manner as if the surgeon had a direct look at the to-be-treated site. Furthermore, absolute measurement can be taken with the invented stereo endoscope. In addition to the previously mentioned decisive improvement for controlled execution of complicated surgical techniques using endoscopic instruments inside cavities, by way of illustration the stomach, bladder, intestines, etc., improved diagnosis can be conducted using the invented stereo endoscope due to the spatial view of the entire interior side of the tube-shaped cavities such as intestinal vessels.

According to the present invention, the solid state image-recorder system attached to the distal end of the endoscope is provided with at least two image recorders which are essentially composed of a lens and a light-sensitive solid state image sensor, by way of illustration a CCD array. The image recorders, which are allocated in pairs, are placed in relation to each other in such a manner that at least the optical axes of the lenses include a convergence angle which can be set, by way of illustration, via controllable microsetting elements. Changing the convergence angle permits, by way of illustration, varying within a certain range the distance between the lens plane and the distant point at which the vision fields of both image-recording systems overlap. Thus, the surgeon is able to adapt the spatial imaging qualities of the optical system optimally to the distance region in front of the lens plane on which the viewing interest is focused, by way of illustration due to a planned surgical procedure using other endoscopic instruments.

A preferred embodiment of the present invention also provides for being able to change the stereo base of the image recorder in such a manner that the spatial viewing qualities can be adapted to the current conditions of the field of vision.

Preferably exits of light conductors, which are disposed in the view direction of the solid state image-recording systems, are used for illuminating the to-be-viewed incorporal areas of the body. Furthermore, a symmetrical arrangement of the light exits about the image-recording systems permits homogeneous illumination which is, in particular, a necessity for stereoscopic images.

Having the image recorders, at least however the solid state image sensors, mechanically disposed perferably on a single conductor plate has proven to be especially advantageous. Such a combination prevents an undesirable maladjustment and ensures undisturbed transmission of the image signals obtained by the image recorder which are converted into electric signals by the solid state image sensors and conducted on along the endoscope shaft via respective lines to a proximally attached video-image processing unit.

The electronic triggering of the solid state image sensors in the form of suited periodic signals, which are necessary for perfect functioning of the sensors, and the delivery of the supply voltage can be conducted for two or more sensors via identical signal lines respectively supply lines because the required input signals for the solid state image sensors are identical. The use of more than one image recorder, therefore, does not result in doubling the input signal lines. Consequently, a minimum endoscopic cross section can be maintained. Only one output signal line has to be provided per image recorder in order to transmit the video-image data to the proximal end.

It has been proven to be advantageous if the periodic signals required for a periodic readout of the solid state image sensors are processed in an electronic processing unit which is disposed in the distal region of the endoscope shaft.

The individual object fields recorded by two image-recording systems are converted as previously discussed into electric signals and conducted on to a proximally attached control, processing and representation unit. The proximal side control unit generates the periods for reading out the image recorder, the processing unit provides dual-channel further processing of the image signals gained by the image recorder, which are then conducted to a representation unit in the form of video signals.

By way of illustration, the video signals of both image-recording systems are transmitted alternately every 50 times a second onto a monitor. With such a monitor, which is viewed through infrared-beam coupled glasses which are equipped with a fluid crystal layer, both recorded object fields appearing alternately on the screen synchronously to the screen frequency can be viewed with the respective eye. By means of synchronous darkening of the glasses, the right eye perceives the image, by way of illustration, of the right image-recording system and in the next tact the left eye perceives the left image-recording system. With a respectively high image-reproduction frequency, the brain processes the visual data into a three-dimensional image. Thus, a three-dimensional image can be generated according to the previously mentioned "one monitor shutter principle". By looking at the screen, the surgeon can view the procedure inside a cavity without effort or eye-straining use of look-through endoscopes while he/she is working with other endoscopic instruments. Surgery is considerably facilitated by the three-dimensional image on the monitor quasi permitting a direct view through the abdomen wall.

The present invention provides that the distal end region of the endoscope having the solid state image-recording system for stereo viewing is designed as a stereo video probe which can be detached from the instrument and which contains a magnetic element by means of which the probe, e.g., using a second external magnet can be positioned and attached by way of illustration to the abdominal wall. In this way, viewing positions can be assumed which could not be reached with a single endoscopic incision without having to make additional incisions. Once the video probe has been inserted inside the body and been fixed beneath, by way of illustration, the abdominal wall by means of an external magnet, the video probe can be brought to any point beneath the abdominal wall by moving the external magnets.

BRIEF DESCRIPTION OF THE DRAWING

The present invention is made more apparent by way of example without the intention of limiting the overall inventive idea using preferred embodiments with reference to the drawing to which explicitly is referred with regard to the disclosure of all the invented details not explained more closely herein. Depicted is in.

DESCRIPTION OF A PREFERRED EMBODIMENT

Figure 1:
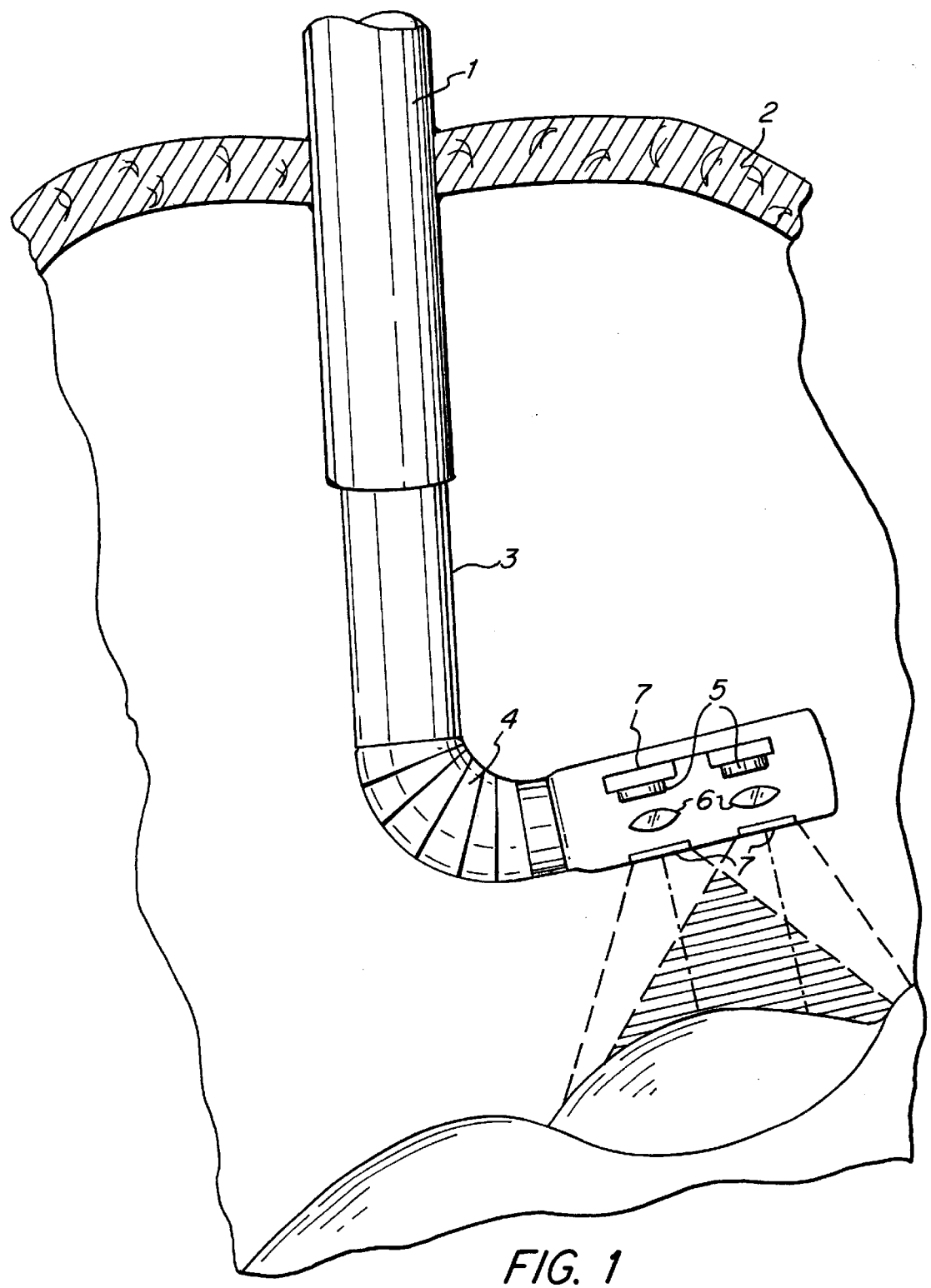
FIG. 1 inside a cavity, a stereo endoscope having an endoscope shaft deflected 90°, FIG. 2 a, b a cross-sectional representation of the invented lateral-view endoscope head, FIG. 3 a, b a lateral view of a stereo lateral-view endoscope having double deflection in the distal region of the endoscope shaft for coaxial alignment of the endoscope shaft in relation to the longitudinal axis of the endoscope and FIG. 4 a cross-sectional representation through the distal endoscope region with straight-ahead and lateral-view optics.

Fig 1. depicts a representation of a cross section showing a stereo lateral-view endoscope which is guided through a trocar tube (1) inside a human body cavity through the abdominal wall (2). After the mobile-designed part of the endoscope shaft (4) protrudes completely out of the trocar tube (1) inside the body, the distal region folds approximately 90° in relation to the longitudinal axis of the endoscope. The folding mechanism can be released, by way of illustration, memory materials having thermal or mechanical memory capacity inserted through the mobile part of the endoscope shaft. Suitably disposed Bowden wires inside the endoscope shaft can also effect the deflection of the distal region.

The image-recording system required for stereo viewing is composed of a pair of identically designed image recorders each of which is provided with a solid state image sensor, (5) before which a lens (6) is attached in viewing direction. The solid state image sensors are disposed on a common conductor plate (7) in order to avoid undesirable maladjustment. The solid state image sensor (5) is usually a CCD array in the form of a chip. However, light-sensitive sensor elements can also by employed, the so-called "die elements", which have no further housing elements.

The solid state image sensors are disposed side-by-side in a row in the axial direction of the endoscope shaft in such a manner that mutual spacing can be varied in almost any region.

Mutual overlapping of both object fields, which are depicted in FIG. 1 as a hatched area, permits a spatial manner of viewing through the endoscope.

If the endoscope at its rigid endoscope shaft (3) is removed once again from the cavity through the trocar tube, the flexible section (4) of the distal region of the endoscope aligns itself again parallel to the axis of the endoscope in such a manner that the orientation of the viewing direction depicted in FIG. 1, which runs coaxially to the axis of the rigid endoscope shaft (3) in the extended state, folds back into a lateral viewing direction. By turning the endoscope shaft about its longitudinal axis, the entire cavity can be viewed in a 360° swing still before the image-recorder head disappears into the trocar tube (1).

Using a transparent material for the trocar tube (1), lateral viewing can be conducted with this device although the distal region of the endoscope is already completely inside the trocar tube. FIG. 2a shows a more distinct cross-sectional representation through the distal region of the endoscope.

The parallel disposed solid state image sensors (5) are disposed jointly on a conductor plate (7). Facing the light-sensitive image sensors (5) are lenses (6) each respectively allocated to a light-sensitive image sensor (5). Lenses (6) image the incident light through the entry window accordingly onto light-sensitive image sensors (5). For illumination of the to-be-examined objects, light-conductor exits (8), which ensure sufficient illumination of both object fields, are provided in the viewing direction symmetrical to the image recorders. By varying the stereo base Sb, the spatial impression can be intensified respectively weakened. For this purpose, the image recorders are disposed in a movable manner to each other.

Figure 2B:
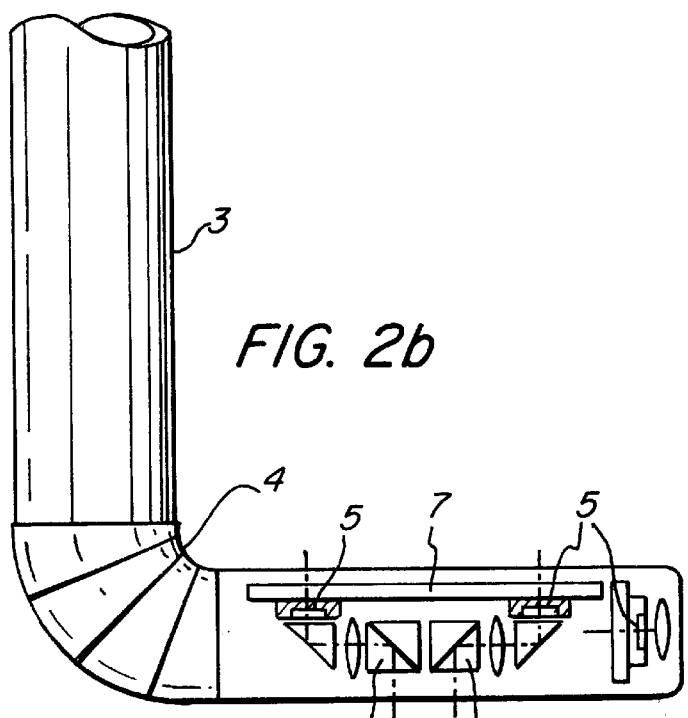
Figure 2A:
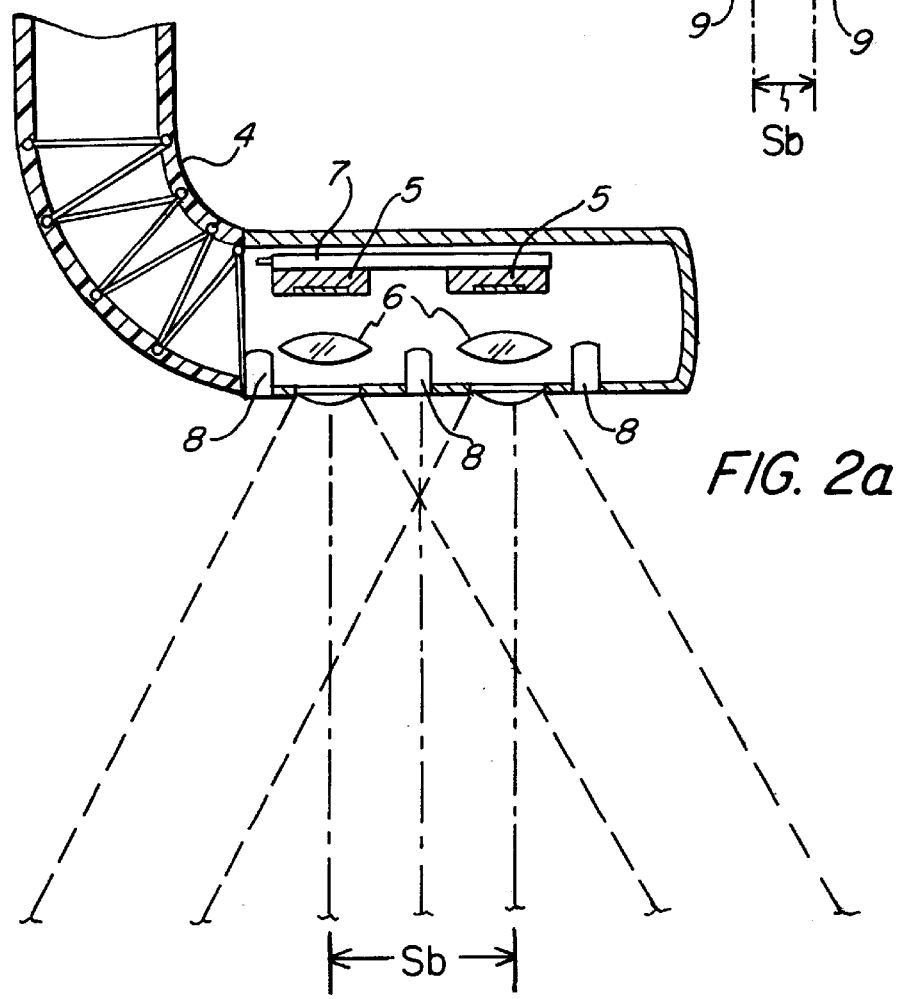

Like FIG. 2a, FIG. 2b shows a cross-sectional representation depicting a modified optical system with which on principle smaller stereo bases can also be realized. The reference numbers stand for the same as in the preceding figures. Using so-called edge prisms (9), the course of the beams can be largely deflected without loss in such a manner that, if solid state image sensors 5 are spaced at a fixed distance from each other, a stereo base Sb deviating from this spacing can be set. Furthermore, an image recorder is disposed in the straight-ahead direction in the arrangement of FIG. 2b.

FIG. 3a shows a lateral view of a stereo endoscope the viewing direction of which runs coaxially to the axis of the rigid endoscope after deflecting twice in the flexible part of the endoscope. Due to the two deflection regions (4), which are provided with deflection lines running in the opposite direction respectively, the distal region of the endoscope which originally was oriented in the lateral viewing direction can be oriented in such a manner that the viewing direction runs through the image recording system coaxially to the axis of the rigid endoscope. Once again the quasi "S-shaped" deflection course in the distal region of the endoscope can be produced by the shaping materials, which by way of illustration possess a memory capacity. The controlled deflection curves can also be achieved via Bowden wires or controllable joints. At least one controllable micro-setting element 20 is operated to displace a respective one of the lenses 5 in order to change a convergence angle between the optical axes of the lenses.

The as such not straight endoscope head is reinserted with the aid of a trocar tube (1) which forces the endoscope shaft to have a straight shape during insertion into a cavity (for this see FIG. 3b). If the distal region protrudes in the thrust directon from the trocar tube, the distal region automatically assumes its prescribed shape in the described manner.

As another special preferred embodiment, guide channels through which, in particular in the deflected state of the distal region, instruments can be inserted into the viewing region (not shown) of the two aforementioned endoscopes. In this way, spatial viewing as well as manipulation with suitable instruments can be conducted with only a single endoscopic operation.

Figure 4:
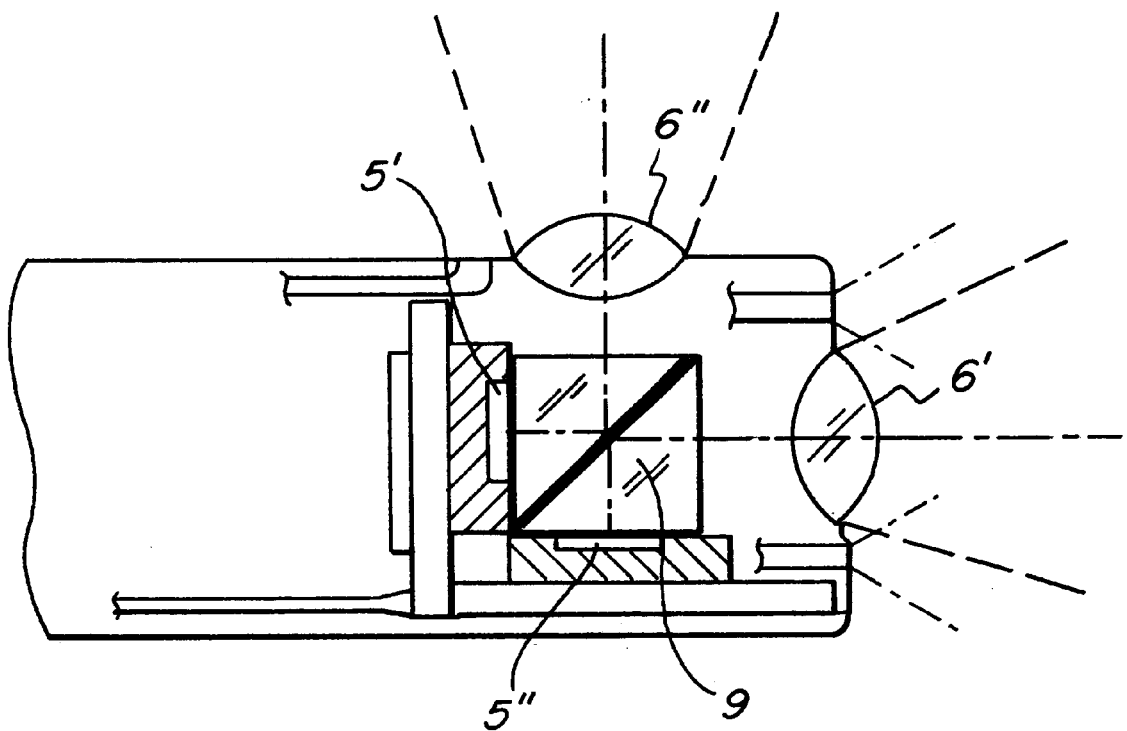

However, it is feasible that numerous image-recording system can be provided in the distal region of the endoscope shaft. FIG. 4 shows, as an especially suited preferred embodiment, an additional image recorder in the straight ahead viewing direction in addition to the image recorders in the lateral viewing direction, permitting simultaneous viewing in both directions.

To two solid state image sensors 5' and 5" lying at a right angle to each other are synchronously transmitted the image of the respective object fields through a beam divider 9 in the form of a square-shaped edge prism by means of the respective lenses 6' and 6". Along with individual image-recording systems, which are only shown in a cross section in FIG. 4, further image-recording systems in the same 90° arrangement should be imagined disposed in a side by side manner.

What is claimed is:

1. An endoscope for examining a corporeal cavity, comprising:
   a trocar sleeve;
   an endoscope shaft having a proximal end portion with a longitudinal axis and a distal end portion with a longitudinal axis, said endoscope shaft being capable of being passed through said trocar sleeve to insert said distal end portion into said corporeal cavity; and
   two solid state image recorders disposed on said distal end portion in a row parallel to said longitudinal axis of said distal end portion and spaced from each other to provide a lateral view stereo-optical system having a viewing direction at generally right angles away from said longitudinal axis of said distal end portion;
   wherein said endoscope shaft has a flexibly bendable portion disposed between said proximal end portion and said distal end portion, so that when said distal end portion and said bendable portion have been passed through said trocar sleeve, said distal end portion may be moved from a first viewing position in which the longitudinal axis of said distal end portion is aligned with the longitudinal axis of said proximal end portion to a second viewing position in which the longitudinal axis of said distal end portion is oriented at generally 90° to an extension of the longitudinal axis of said proximal end portion, with the viewing direction of said stereo-optical system being parallel to the extension of the longitudinal axis of said proximal end portion.

2. An endoscope according to claim 1, wherein said two side-by-side solid state image recorders have solid state image sensors disposed on a single conductor plate.

3. An endoscope according to claim 2, wherein said solid state image sensors are one of semiconductor chips and CCD arrays disposed on a single ceramic carrier.

4. An endoscope according to claim 1, further comprising an additional image recorder being provided in said endoscope shaft in said distal end portion of said endoscope so as to provide a viewing direction along the longitudinal axis of said endoscope.

5. An endoscope according to claim 1, wherein said solid state image sensors enable recording and reading out of image data requiring several periodic signals and supply voltages as input signals and delivering at least one output signal containing the image data.

6. An endoscope according to claim 5, wherein for each said solid state image sensor an output signal line is required for image data transmission from the distal end region to a proximal region of said endoscope for further processing.

7. An endoscope according to claim 5, further comprising an electronic processing unit provided in said endoscope shaft in said distal end region for processing the periodic signals required for reading out said solid state image sensors.

8. An endoscope according to claim 7, wherein said electronic processing unit enables joint processing and delivery of the periodic signals in common to two or more solid state image sensors.

9. An endoscope according to claim 1, further comprising identical input signals for two or more solid state image sensors so that the number of signal lines for said input signals from a proximal side supply unit to a distal instrument tip remains constant for more than one sensor.

10. An endoscope according to claim 1, wherein the at least two solid state image recorders provide an electrical output to a proximal region of the endoscope representing an image viewed by the lateral view optics thereof.

11. An endoscope for examining a corporeal cavity, comprising:
    an endoscope shaft having a proximal end portion with a longitudinal axis and distal end portion with a longitudinal axis, said endoscope shaft being capable of being passed through a trocar sleeve to insert said distal end portion into said corporeal cavity; and
    two solid state image recorders disposed on said distal end portion in a row parallel to said longitudinal axis of said distal end portion and spaced from each other to provide a lateral view stereo-optical system having a viewing direction at right angles away from said longitudinal axis of said distal end portion;
    wherein
    said endoscope shaft has two flexibly bendable portions disposed in succession between said proximal end portion and said distal end portion, said two bendable portions being bendable in opposite directions, respectively, so that when said distal end portion and said bendable portion have been passed through said trocar sleeve, said distal end portion may be moved from a first viewing position in which the longitudinal axis of said distal end portion is aligned with the longitudinal axis of said proximal end portion to a second viewing position In which the longitudinal axis of said distal end portion is oriented at generally 90° to and passes through an extension of the longitudinal axis of said proximal end portion, with the viewing direction of said stereo-optical system being directed along said extension of the longitudinal axis of said proximal end portion.

12. The endoscope according to claim 11 further comprising a bendable element connected to the distal end to provide a relative pivotal motion between the proximal and distal ends and selected from the group consisting of Bowden wires, controllable joints, and a bendable portion having mechanical or thermal memory capacity, the endoscope further comprising a pair of deflecting optical elements axially aligned with and positioned between the solid state image recorders to provide a middle point for stereo viewing.

13. An endoscope according to claim 1 or 11, wherein said two solid state image recorders have converging optical axes so that object fields viewed by each of said image recorders are identical.

14. An endoscope according to claim 1, wherein said distal end portion is moved from said first viewing position to said second viewing position by means selected from the group consisting of Bowden wires, controllable joints, and a component composed of a material having mechanical or thermal memory capacity.

15. An endoscope according to claim 13, wherein each of said solid state image recorders is provided with a solid state image sensor and imaging optics.

16. An endoscope according to claim 15, wherein said solid state image sensors are mechanically connected.

17. An endoscope according to claim 13, wherein a convergence angle of said optical axes is adjustable.

18. An endoscope according to claim 13, wherein said distal end portion is provided with light-conductor exits which are directed along said viewing direction and disposed symmetrically with respect to said two solid state image recorders and illuminate an object field.

* * * * *